US006391909B1

(12) United States Patent
Makriyannis et al.

(10) Patent No.: US 6,391,909 B1
(45) Date of Patent: *May 21, 2002

(54) ANANDAMIDE INHIBITORS AS ANALGESIC AGENTS

(75) Inventors: Alexandros Makriyannis, Ashford; Sonyan Lin, Storrs; William Adam Hill, Ashford, all of CT (US)

(73) Assignee: University of Connecticut, Farmington, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/553,499

(22) Filed: Apr. 20, 2000

Related U.S. Application Data

(63) Continuation of application No. 09/250,698, filed on Feb. 16, 1999, now abandoned, which is a continuation of application No. 08/967,847, filed on Nov. 12, 1997, now Pat. No. 5,874,459, which is a continuation of application No. 08/658,949, filed on May 31, 1996, now Pat. No. 5,688,825.

(51) Int. Cl.⁷ .................... A61K 31/166; A61K 31/24; A61K 31/4015; A61K 31/10; C07C 233/01
(52) U.S. Cl. ............... 514/425; 514/428; 514/507; 514/534; 514/621; 514/622; 514/627; 514/710; 564/123
(58) Field of Search .................. 514/428, 425, 514/534, 627, 710, 507, 621, 622; 564/123

(56) References Cited

U.S. PATENT DOCUMENTS

| | | | | |
|---|---|---|---|---|
| 3,465,024 A | | 9/1969 | Brownstein et al. | 260/453 |
| 3,577,458 A | | 5/1971 | Brownstein et al. | 260/545 |
| 5,688,825 A | * | 11/1997 | Makriyannis et al. | 514/423 |
| 5,874,459 A | * | 2/1999 | Makriyannis et al. | 514/423 |

FOREIGN PATENT DOCUMENTS

EP        0737671 A2    10/1996

OTHER PUBLICATIONS

Cherest, M. et al., "The Action of Acetyl Chloride and of Acetic Anhydride on the Lithium Nitronate Sale of 2–Phenylnitoethane. Reactivity of the Intermediate Nitril Oxide as an Electrophile or as a Dipole, depending on the Nature o the Medium," *Tetrahedron Letters*, 42(14) :3825–3840 (1986) (English Abstract).

Demuynck, L. et al., "Rearrangement of Indolo [2,3–a] Quinolizidines to Derivatives with E–Azaaspidospermane Skeleton," *Tetrahedron Letters*, 30(6) :719–722 (1989). (English Abstract).

Neunhoeffer, O. et al., "Acylating Activity of O–Acylated Hydroxylamine Derivatives," *Justus Liebigs Ann. Chem.*, 736:100–109 (1970). (English Abstract).

Cherest, M. et al., "A Novel Electrophilic N–Amidation Via Electron Deficient Complexes: Action of Ferric Chloride on N–Acetyloxyamides," *Tetrahedron Letters*, 30 (6): 715–718 (1989).

Deutsch, D.G. and Chin, S.A., "Enzymatic Synthesis and Degradation of Anandamide, A Cannabinoid Receptor Agonist," *Biochemical Pharmacology*, 46 (5): 791–796 (1993).

Smith, P.B. et al., "The Pharmacological Activity of Anandamide, a Putative Endogenous Cannabinoid, in Mice," *J. Pharm. and Exp. Therap.*, 270 (1): 219–227 (1994).

Horrevoets, A.J.G. et al., "Inactivation of *Escherichia coli* Outer–Membrane Phospholipase A by the Affinity Label Hexadecanesulfonyl Fluoride," *Eur. J. Biochem.*, 198: 247–253 (1991).

Kawase, M. et al., "Electrophilic Aromatic Substitution with N–Methoxy–N–acylnitrenium Ions Generated from N–Chloro–N–methoxamides: Syntheses of Nitrogen Heterocyclic Compounds Bearing a N–Methoxyamide Group," *J. Org. Chem.*, 54: 3394–3403 (1989).

Koutek, B. et al., "Inhibitors of Arachidonoyl Ethanolamide Hydrolysis," *J. Biol. Chem.*, 269(37): 22937–22940 (1994).

Fride, E. and Mechoulam R., "Pharmacological Activity of the Cannabinoid Receptor Agonist, Anandamide, a Brain Constituent," *European Journal of Pharmacology*, 231: 313–314 (1993).

Abadji, V., et al., "(R)–Methanandamide: A Chiral Novel Anandamide Processing Higher Potency and Metabolic Stability," *J. Med. Chem. 37*: 1889–1893 (1994).

Deutsch, D.G., et al., "Fatty Acid Sulfonyl Fluorides Inhibit Anandamide Metabolism and Bind to the Cannabinoid Receptor," *Biochem. Biophys. Res. Commun. 231*: 217–221 (1997).

* cited by examiner

Primary Examiner—T. A Solola
(74) *Attorney, Agent, or Firm*—Alix, Yale & Ristas, LLP (57) ABSTRACT

Disclosed is a method of inhibiting anandamide amidase in an individual or animal and novel inhibitors of anandamide amidase. The disclosed method can be used to reduce pain in an individual or animal suffering from pain, reducing nausea in an individual undergoing chemotherapy, suppressing appetite in an individual, reducing intraocular pressure in the eye of an individual or animal suffering from glaucoma and suppressing the immune system in an individual with an organ transplant.

18 Claims, 5 Drawing Sheets

ANANDAMIDE INHIBITORS AS ANALGESIC AGENTS

RELATED APPLICATIONS

This application is a Continuation of U.S. application Ser. No. 09/250,698 filed Feb. 16, 1999, abandoned, which is a continuation of U.S. application Ser. No. 08/967,847 filed Nov. 12, 1997, now U.S. Pat. No. 5,874,459, which is a continuation of U.S. application Ser. No. 08/658,949 filed May 31, 1996, now U.S. Pat. No. 5,688,825, the contents of which are incorporated herein by reference in their entirety.

GOVERNMENT FUNDING

This invention was made with Government support under Contract Nos. DA 3801 awarded by the National Institute of Drug Abuse. The Government has certain rights in the invention.

BACKGROUND $\Delta^9$-Tetrahydrocannabinol, the pyschoactive marijuana derived cannabinoid, binds to the CB1 receptor in the brain and to the CB2 receptor in the spleen. Compounds which stimulate the CB1 receptor have been shown to induce analgesia and sedation, to cause mood elevation, to control nausea and appetite and to lower intraocular pressure (Mechoulam, *Cannabinoids as Therapeutic Agents*, CRC Press, Boca Raton, Fla. (1986), Fride and Mechoulam, *Eur. J. Pharmacol.* 231:313 (1993), Crawley et al., *Pharmacol. Biochem. Behav.* 46:967 (1993) and Smith et al., *J. Pharm. Exp. Therap.* 270:219 (1994)). Cannabinoids have also been shown to suppress the immune system (Mechoulam, *Cannabinoids as Therapeutic Agents*, CRC Press, Boca Raton, Fla. (1986). Thus, compounds which stimulate the CB1 or CB2 receptor, directly or indirectly, are potentially useful in treating glaucoma, preventing tissue rejection in organ transplant patients, controlling nausea in patients undergoing chemotherapy, controlling pain and enhancing the appetite and controlling pain in individuals with AIDS Wasting Syndrome.

Arachidonyl ethanolamide (anandamide) is a naturally-occurring brain constituent that acts as a CB1 and CB2 agonist and exhibits pharmacological activity in mice comparable to cannabinoids (Fride and Mechoulam (1993), Crawley et al. (1993) and Smith et al. (1994)). Anandamide is cleaved in vivo by anandamide amidase. Thus, inhibitors of anandamide amidase have the effect of indirectly stimulating the CB1 and CB2 receptors by increasing in vivo levels of anandamide.

In addition to acting at the CB1 and CB2 receptors, cannabinoids also affect cellular membranes, thereby producing undesirable side effects such as drowsiness, impairment of monoamide oxidase function and impairment of non-receptor mediated brain function. The addictive and psychotropic properties of cannabinoids also limit their therapeutic value. Inhibitors of anandamide amidase are not expected to have the undesired membrane-related side-effects produced by cannabinoids. By providing an alternate mechanism for stimulating the CB1 and CB2 receptor, anandamide inhibitors might not have the addictive and psychotropic properties of cannabinoids. However, present inhibitors of anandamide amidase have disadvantages. For example, phenylmethylsulfonyl fluoride (PMSF) is toxic to cells. Thus, there is a need for new and more potent inhibitors of anandamide amidase which have reduced toxicity towards cells and which do not significantly interact with the CB1 or CB2 receptor at inhibitory concentrations.

SUMMARY OF THE INVENTION

It has now been found that long chain fatty acids and aromatic acid analogs of long chain fatty acids with head groups capable of irreversibly binding to a nucleophilic group at an enzyme active site are potent inhibitors of anandamide amidase. For example, palmitylsulfonyl fluoride was found to increase the level of undegraded anandamide 55-fold at 10 nM in intact neuroblastoma cells (Example 1) and is therefore more than 100 fold more potent than phenylmethylsulfonyl fluoride at inhibiting anandamide amidase. At the same time, the inhibitors disclosed herein have a low affinity for the CB1 receptor (Example 3). For example, the binding affinity of palmitylsulfonyl fluoride for the CB1 receptor is about 10 times lower than anandamide. In addition, it has been found that palmitylsulfonyl fluoride causes some of the same pharmacological effects in rats as do compounds which stimulate the CB1 receptor directly, such as $\Delta^9$-tetrahydrocannabinol. For example, palmitylsulfonyl fluoride is shown herein to induce analgesia in rats (Example 4). Based on these results, methods of inhibiting anandamide amidase, thereby stimulating the CB1 and CB2 receptors, in an individual or animal are disclosed. Also disclosed are novel compounds which inhibit anandamide amidase.

The present invention is a method of inhibiting anandamide amidase in an individual or animal. The method comprises administering to the individual or animal a therapeutically effective amount of a compound represented by Structural Formula I:

$$R\text{—}X\text{—}Y \qquad (I)$$

and physiologically acceptable salts thereof.

R is selected from the group consisting of a methyl group, an aryl group, a substituted aryl group, a heteroaryl group, a substituted heteroaryl group, a heterocyclic group and a substituted heterocyclic group.

X is a straight chain hydrocarbyl group or a substituted straight chain hydrocarbyl group containing from about 4 to about 18 carbon atoms if R is an aryl group, a substituted aryl group, a heteroaryl group, a substituted heteroaryl group, a heterocyclic group or a substituted heterocyclic group.

X is a hydrocarbyl group or a substituted hydrocarbyl group containing from about 10 to about 24 carbon atoms if R is a methyl group.

Y is a moiety capable of irreversibly binding with a nucleophilic group at the active site of an amidase enzyme.

The method and the novel compounds disclosed herein have therapeutic uses. For example, the compounds and methods of the present invention, like cannabinoids, can relieve the pain caused by cancer and the nausea resulting from cancer chemotherapy. They are not expected to have the undesirable membrane-related side-effects associated with cannabinoids. In addition, the methods and compounds disclosed herein are expected to be immunosuppressive and can therefore be used to prevent organ rejection in an individual undergoing an organ transplant. Because the compounds and methods of the present invention enhance the appetite of an individual, they can be used treat patients with AIDS Wasting Syndrome, who are often suffering from malnourishment as a result of appetite loss.

The novel inhibitors of anandamide amidase disclosed herein also have research uses. For example, they can be used to maintain the level of anandamide in vitro to study the effect of ananamide on cells and to maintain the level of anandamide in vivo to study the effect of anandamide on individuals and animals. They can be used to characterize cells, for example to determine if a cell type has cannabimetic or amidase activity. For example, the inhibitors can be used to determine if a cell population expresses anandamide amidase by contacting the cells with an inhibitor and then determining if there is an increase in the concentration of anandamide. The anandamide inhibitors disclosed herein can also be used as in aid in drug design, for example as a control in assays for testing other compounds for their ability to inhibit anandamide amidase and to determine the structure activity requirements of anandamide amidase inhibitors.

DETAILED DESCRIPTION OF THE INVENTION

One embodiment of the present invention is directed to a method of inhibiting anandamide amidase in an individual or animal. The inhibition of anandamide amidase results in increased levels of anandamide in the individual or animal, thereby causing increased stimulation of cannabinoid receptors in the individual or animal, e.g., the CB1 receptor in the brain and the CB2 receptor in the spleen. Thus, the present invention is also a method of stimulating cannabinoid receptors in an individual or animal. It is to be understood that the present invention can also be used to stimulate receptors not yet discovered for which anandamide and/or a cannabinoid acts as an agonist.

"Y" in Structural Formula I is a moiety capable of irreversibly binding with a nucleophilic group at the active site of an amidase enzyme. Thus, Y is capable of forming a stable covalent bond with the nucleophilic group at the active site of an amidase enzyme. Suitable structures for Y therefore do not encompass moieties, such as trifluoromethyl ketones, which are capable of acting as a transition state analog of an amidase enzyme and which bind reversibly to these enzymes. As used herein, an "amidase" is an enzyme involved in the hydrolysis of an amide bond.

A nucleophilic group at the active site of an amidase enzyme is a heteroatom-containing functional group on the side chain of an amino acid found at the enzyme active site and includes the hydroxyl group of serine or threonine, the thiol group of cysteine, the phenol group of tyrosine and the amino group of lysine, ornithine or arginine or the imidazole group of histidine.

Examples of suitable structures for Y include:

R1 is selected from the group consisting of —F and —O(C1 to C4 straight or branched chain alkyl group). R2 is a C1 to C4 straight or branched chain alkyl group.

As used herein, "a straight chain hydrocarbyl group" includes a polyalkylene, i.e., —$(CH_2)_n$—. "n" is a positive integer from about 10 to about 24, when R is methyl, and from about 4 to about 18, when R is aryl, substituted aryl, heteroaryl, substituted heteroaryl, heterocyclic or substituted heterocyclic. A straight chain hydrocarbyl group also includes two or more polyalkylene groups connected by one or more ether, thioether ether, cis-alkenyl, trans-alkenyl or alkynyl linkage such that the total number of methylene carbon atoms is from about 10 to about 24 when R is methyl and from about 4 to 18 when R is aryl, substituted aryl, heteroaryl, substituted heteroaryl, heterocyclic or substituted heterocyclic. Examples include —$(CH_2)_m$—O—$(CH_2)_o$—, —$(CH_2)_m$—S—$(CH_2)_o$—, —$(CH_2)_m$—CH=CH—$(CH_2)_o$—, —$(CH_2)_m$—C≡C—$(CH_2)_o$—, wherein m and o are each a positive integer such that the sum of m and o is equal to n. Specific examples include where X is —$(CH_2)_4$-(cis—CH=CHCH_2—)_4$—$CH_2CH_2$—, —$(CH_2)_4$-(cis—CH=CHCH_2)_3$—$(CH_2)_5$— and where R—X— is a docosatetraenyl or a homo-γ-linolenyl moiety.

In one aspect of the present invention, R in the compound being administered to inhibit anandamide amidase is methyl and Y is sulfonyl fluoride or a C1 to C4 straight or branched chain sulfonyl ester. Preferably, Y is a sulfonyl fluoride. Specific examples of sulfonyl fluorides and sulfonyl esters include where R—X— is archidyl, $\Delta^8,\Delta^{11},\Delta^{14}$-eicosatrienyl, docosatetraenyl, homo-γ-linolenyl and $CH_3$—$(CH_2)_n$—, wherein n is 10 (lauryl), 11, 12 (myristyl), 13, 14 (palmityl), 15 or 16 (stearyl).

As used herein, an "aryl" group is a carbocyclic aromatic ring system such as phenyl, 1-naphthyl or 2-naphthyl. A "heteroaryl" group is aromatic ring system containing one or more heteroatoms such as nitrogen, oxygen or sulfur. Examples of heteroaryl groups include 2-furanyl, 3-furanyl, 2-thienyl, 3-thienyl, 2-pyridinyl, 3-pyridinyl, 4-pyridinyl, 2-pyrimidinyl, 4-pyrimidinyl, 5-pyrimidinyl, 3-pyrazolyl, 4-pyrazolyl, 5-pyrazolyl, 2-pyrazinyl, 2-imidazolyl, 4-imidazolyl, 1-pyrrolyl, 2-pyrrolyl, 2-oxazolyl, 4-oxazolyl, 5-oxazolyl, 2-thiazolyl, 4-thiazolyl and 5-thiazolyl. "Heteroaryl" groups also include fused polycyclic systems in which one or more monocylic aryl or monocyclic heteroaryl group is fused to another heteroaryl group. Examples include 2-benzothienyl, 3-benzothienyl, 2-benzofuranyl, 3-benzofuranyl, 2-indolyl, 2-quinolinyl and 3-quinolinyl.

As used herein, a "heterocyclic" group is a C5–C8 non-aromatic ring system containing one or more heteroatoms such as oxygen, nitrogen or sulfur. Examples include 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 3-piperazinyl, 1-piperidinyl, 2-piperidinyl, 3-piperidinyl, 4-piperidinyl and 4-thiazolidinyl.

Suitable substituents on a straight chain hydrocarbyl group include methyl, ethyl, hydroxy, hydroxymethyl, thiol, methoxy, ethoxy and hydroxy. Suitable substituents on an aryl, heteroaryl or heterocyclic group include groups such as lower alkyl, aryl, heteroaryl, (lower alkoxy)—O—, (aryl or substituted aryl)—O—, halo, —CO—O(lower alkyl), —CHO, —CO—(lower alkyl), —CO—NH(lower alkyl), —CO—N(lower alkyl)$_2$, —NO$_2$, —CF$_3$, —CN, and (lower alkyl)—S—. A lower alkyl group is a C1 to about C5 straight or branched chain alkyl group.

The present invention also refers to novel compounds which can be used to inhibit anandamide amidase. In one embodiment, the compound has a structure represented by Structural Formula (II):

(II)

and physiologically acceptable salts thereof. R1 is —F or (C1 to C4 alkyl)O—. R and X are as defined above for Structural Formula (I).

In another embodiment, the novel compound of the present invention has a structure represented by Structural Formula (III):

(III)

and physiologically acceptable salts thereof.

R' is selected from the group consisting of an aryl group, a substituted aryl group, a heteroaryl group, a substituted heteroaryl group, a heterocyclic group and a substituted heterocyclic group.

R2 is a C1 to C4 straight or branched chain alkyl group.

p is an integer from about 6 to about 18. In another aspect, p is an integer from about 10 to about 18.

A "therapeutically effective amount" of a compound, as used herein, is the quantity of a compound which, when administered to an individual or animal, results in a sufficiently high level of anandamide in the individual or animal to cause a discernable increase or decrease in a cellular activity affected or controlled by cannabinoid receptors. For example, anandamide can stimulate receptor-mediated signal transduction that leads to the inhibition of forskolin-stimulated adenylate cyclase (Vogel, et al., J. Nurochem. 61:352 (1993). Anandamide also causes partial inhibition of N-type calcium currents via a pertussis toxin-sensitive G protein pathway, independently of cAMP metabolism (Mackie et al., Mol. Pharmacol. 47:711 (1993)).

A "therapeutically effective amount" of an anandamide inhibitor can also be an amount which results in a sufficiently high level of anandamide in an individual or animal to cause a physiological effect resulting from stimulation of cannabinoid receptors. Physiological effects which result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1000 mg/day.

As used herein, an "individual" refers to a human. An "animal" refers to veterinary animals, such as dogs, cats, horses, and the like, and farm animals, such as cows, pigs, guinea pigs and the like.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

General methods of preparing the sulfonyl fluorides, the N-[(alkyl-sulfonyl)oxy] succinimides and the N-O-diacylhydroxylamines of the present invention are provided in Example 5, Example 6 and Example 7, respectively.

The invention will now be further and specifically described by the following examples.

EXEMPLIFICATION

Example 1

Increased [$^3$-H]Anandamide Levels in Neuroblastoma Cells in the Presence of Palmityl Sulfonyl Fluoride The assay of the anandamide amidase in intact neuroblastoma cells was performed as described previously (Deutsch, D. G. and S. A. Chin, Biochem. Pharmacol. 46:791–796 (1993)). The experiments were performed with 4×10$^6$ neuroblastoma cells (N18TG2)/6-cm dish. Experimental cells were incubated in 2 ml of media, consisting of Ham's F-12/Dulbecco's modified Eagle's medium (Life Technologies, Inc.) with penicillin, streptomycin, and gentamicin plus 10% bovine calf serum (HyClone, Logan, Utah), plus the indicated concentration of inhibitor for 20 minutes. All cells were grown at 37° in a humidified atmosphere containing 5% CO$_2$ in air. [$^3$H]Anandamide (0.2 μCi of 221 Ci/mmol of [$^3$H]anandamide) was added and the incubation continued for 1 hour. Control cells contained no inhibitor. At the end of the incubation, the cells were washed once with cell culture media and removed from the plates, after a brief incubation with 2 ml of 0.05% trypsin in 0.53 mM EDTA solution at 37° C. The amounts of [$^3$H] anandamide, [$^3$H]phospholipids, and [$^3$H]arachidonate in the cells and media were quantified by liquid scintillation counting of the silica scraped from the appropriate areas of the plate after quenching the reaction with chloroform methanol (1:1), extraction of the sample from the organic phase, and TLC analysis on channeled silica gel-coated plates, with a solvent system consisting of the organic layer of an ethyl acetate:hexane:acetic acid:water (100:50:20:100) mixture.

Figure 1:
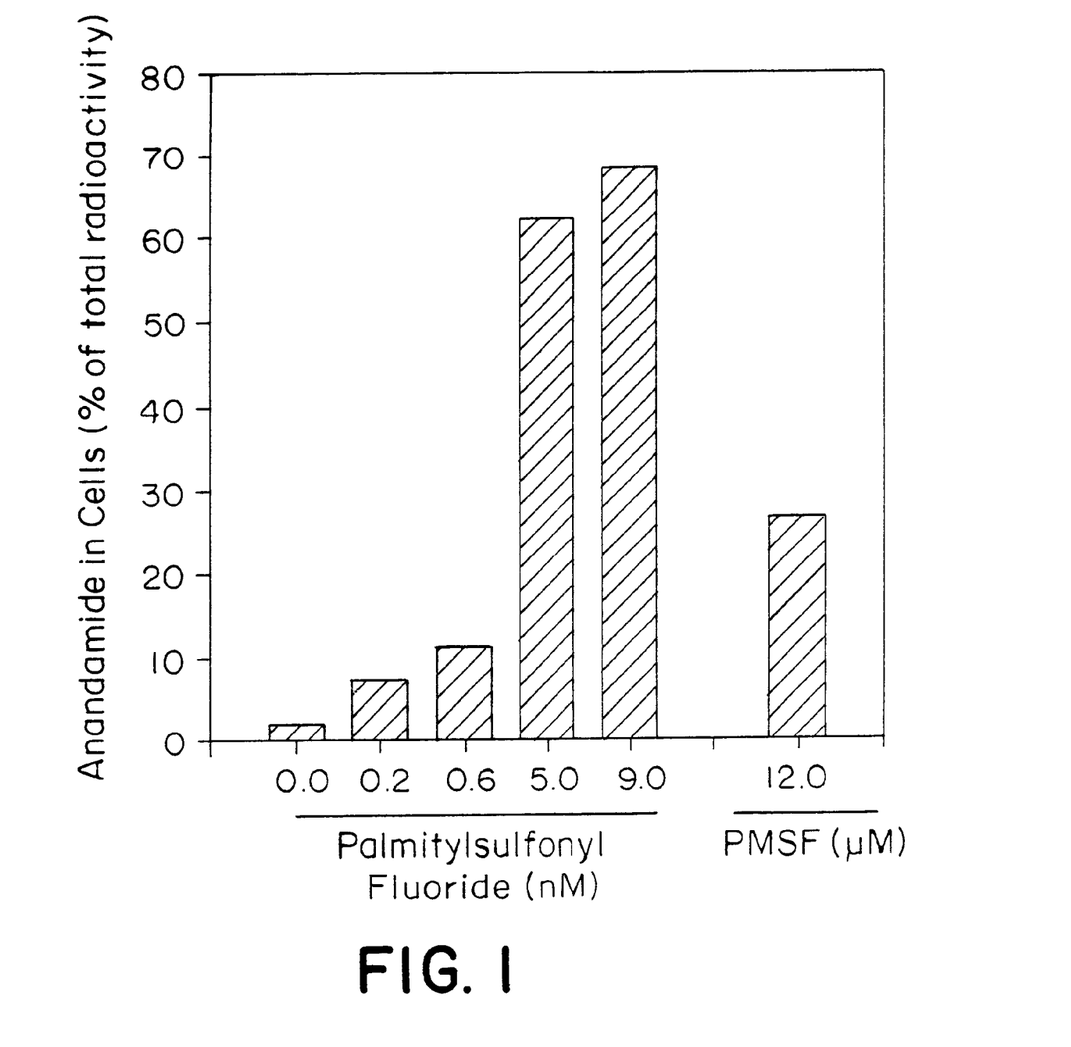
FIG. 1 is a graph showing the effect of palmitylsulfonyl fluoride and phenylmethylsulfonyl fluoride on anandamide levels in neuroblastoma cells (N18TG2).
Figure 2A:
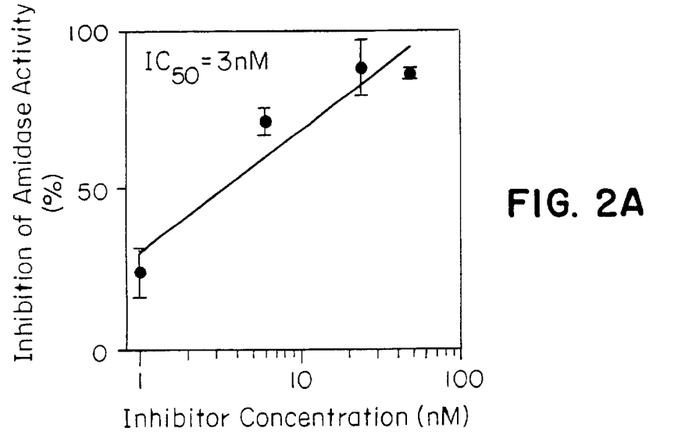
FIGS. 2A–2E are graphs showing the $IC_{50}$ values for the inhibition of anandamide amidase by (A) laurylsulfonyl fluoride; (B) myristylsulfonyl fluoride; (C) palmitylsulfonyl fluoride; (D) stearylsulfonyl fluoride; and (E) arachidylsulfonyl fluoride.
Figure 2B:
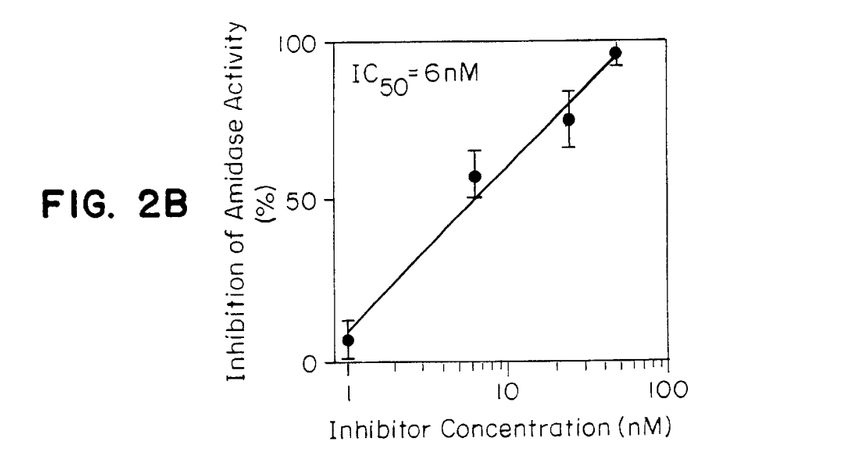
Figure 2C:
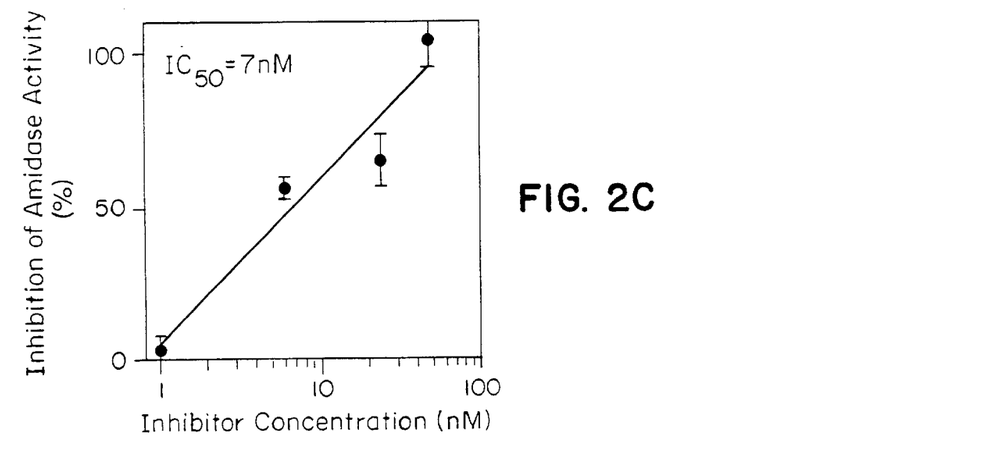
Figure 2D:
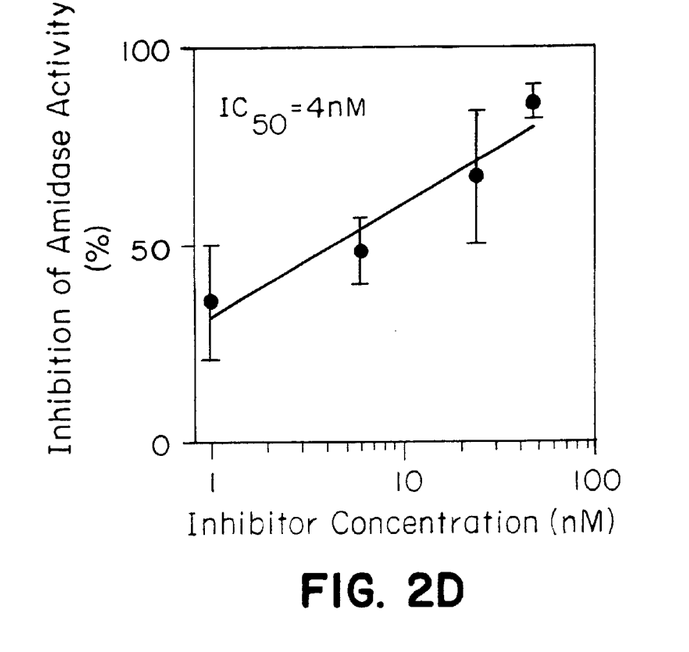
Figure 2E:
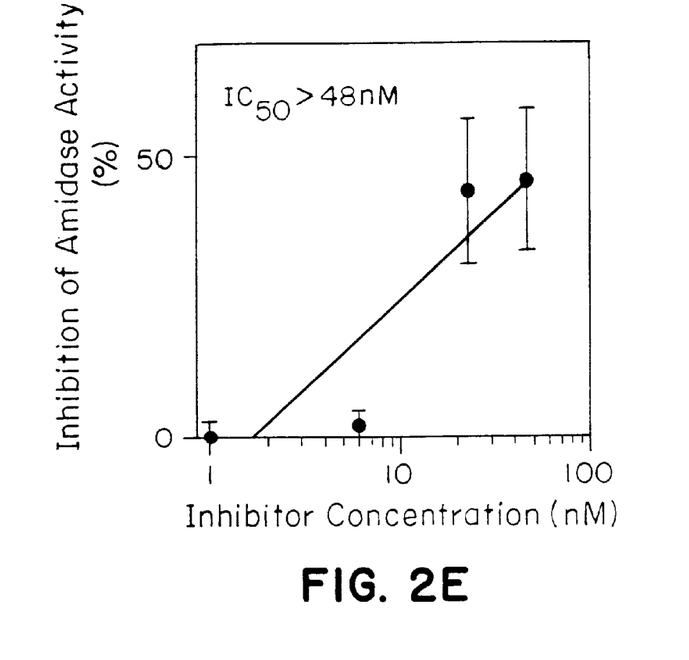

The level of [$^3$H] anandamide found in the neuroblastoma cells incubated with palmitylfsulfonyl fluoride, with phenylmethylsulfonyl fluoride and in control cells is shown in FIG. 1. Nanomolar amounts of palmitylsulfonyl fluoride were sufficient so that over 50% of the radioactivity was found in anandamide, rather than in anandamide cleavage products such as arachidonate. This result indicates that palmitylfsulfonyl fluoride is highly effective at inhibiting anandamide amidase. Concentrations greater than 10 micromolar of phenylmethylsulfonyl fluoride were required to achieve comparable levels of anandamide amidase inhibition. Almost complete degradation of [$^3$H] anandamide was observed in control cells.

Example 2

Determination of $IC_{50}$ Values for Sulfonyl Fluoride Inhibitors of Anandamide Amidase The assay of the anandamide amidase in vitro was performed as described previously (Deutsch, D. G. and S. A. Chin, *Biochem. Pharmacol.* 46:791–796 (1993)). The indicated amount of each compound was preincubated in a buffer consisting of 300 μg of crude rat brain homogenate protein, 500 μg/ml fatty acid-free bovine serum albumin, in phosphate-buffered saline in a final volume of 1.0 ml, for 10 minutes at 37° C. Crude rat brain homogenate was obtained by decapitating female adult Sprague-Dawley rats, dissecting the desired tissue and homogenizing in five volumes of ice-cold TE (10 mM Tris-HCl, 1 mM EDTA, pH 7.6). Substrate (27.7 μM anandamide+0.2 μCi of 221 Ci/mmol [$^3$H]anandamide ([arachidonyl-5,6,8,9,11,12,14,15-$^3$H] ethanolamide)) (obtained from the National Institute on Drug Abuse) was then added and the samples incubated for 10 minutes. The reaction was quenched by the addition of chloroform:methanol (1:1) and enzyme activity was analyzed by TLC as described in Example 1.

The results for laurylsulfonyl fluoride, myristylsulfonyl fluoride, palmitylsulfonyl fluoride, stearylsulfonyl fluoride and arachidylsulfonyl fluoride are shown in FIG. 2. All compounds were effective inhibitors of anandamide amidase. All compounds except arachidylsulfonyl fluoride had an $IC_{50}$ of less than 10 nM. Arachidylsulfonyl fluoride was an effective inhibitor of anandamide amidase at concentrations less than 100 nM.

Example 3

Palmitylsulfonyl Fluoride Binds Less Efficiently to the CB1 Receptor than Anandamide For the CBR1 ligand binding determinations, brain membranes were prepared from frozen rat brains according to the procedure published by Devane et al. (Devane, W. A., et al., *Mol. Pharmacol.* 34:605–613 (1988)). Quantitation of the binding of the fatty acid analogs to CB1 was performed by incubating the analogs at the indicated concentration with 30 μg of membrane protein in a buffer containing 500 pm of the bicyclic cannabinoid analog [$^3$H]CP-55940, 20 mM Tris-Cl, pH 7.4, 3 mM $MgCl_2$, 1 mM Tris-EDTA, and 0.135 mg/ml fatty acid-deficient bovine serum albumin in a final volume of 200 μl in Regisil-treated glass tubes. Specific binding was defined as that which could be displayed by 100 nM desacetyllevonantradol. After 60 minutes at 30° C., the incubation was terminated by the addition of 250 μl of 50 mg/ml bovine serum albumin and the immediate filtration over GF/B filters and washing with ice cold buffer (20 mM Tris-Cl, pH 7.4, 2 mM $MgCl_2$). The filters were treated with 0.1% sodium dodecyl sulfate prior to addition of scintillation mixture and counting in a liquid scintillation counter.

Figure 3:
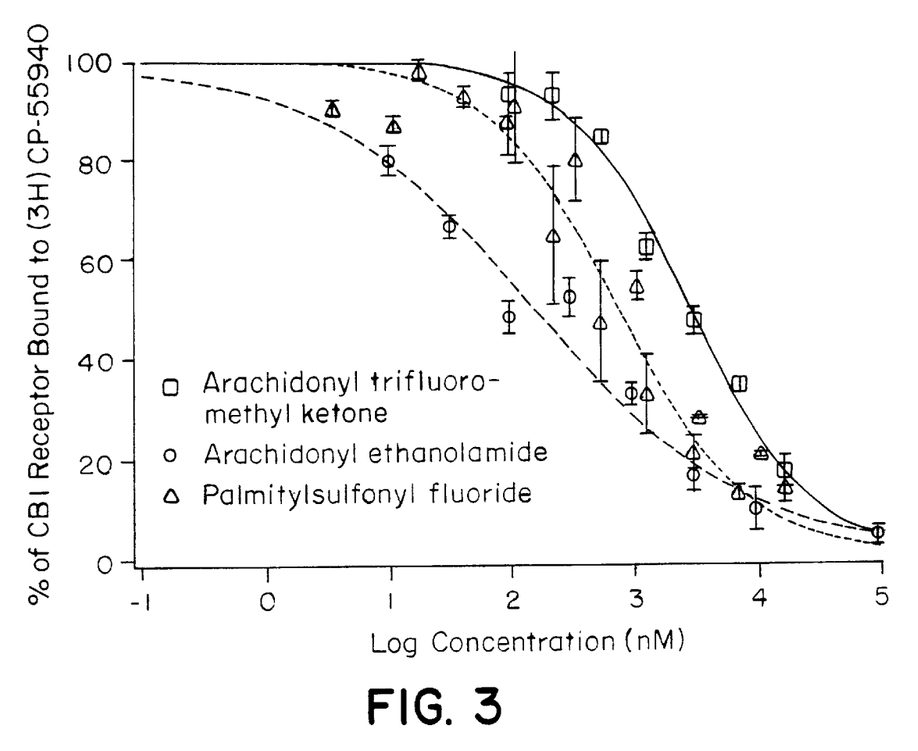
FIG. 3 is a graph showing the log dose-response curves for palmitylsulfonyl fluoride ($K_i$ as 350.4), arachidonyl trifluoromethyl ($K_i$ is 1325) ketone and arachidonoyl ethanolamide ($K_i$ is 70.03) in competition with [H³]CP-55940 binding to CB1.

The log dose-response curve for palmitylsulfonyl fluoride, arachidonyl trifluoromethyl ketone and arachidonoyl ethanolamide in competition with [$^3$H]CP-55940 binding CB1 is shown FIG. 3. This figure shows that palmitylsulfonyl fluoride binds to the CB1 receptor with less than 10% the efficiency of arachidonoyl ethanolamide.

Example 4

Palmitylsulfonyl Fluoride Induces Analgesia in Rats

Drug mixture were prepared by mixing with two parts Tween 80 by weight and dispersing into 0.9% w/v aqueous NaCl solution (saline) as described previously for $\Delta^9$-THC (Pertwee et al., *Br. J. Pharmacol.* 105:980 (1992)).

Drug mixtures were injected intravenously into male MF1 mice weighing 23–29 grams. Analgesia was measured by means of a "rat flick test" in which the time taken for a lightly restrained mouse to flick it tail away from a radiant heat stimulus was noted. The methods is based on the test described by D'Amour and Smith (D'Amour, F. E., Smith, D. L., *J. Pharmacol. Exp. Ther.,* 72:74–79 (1941)). Mice were subjected to the tail flick at −30 minutes (control latency) and at 12 minutes (test latency). The maximum possible tail flick latency was 10 s as mice that did not respond within this time were removed from the apparatus to prevent tissue damage. Analgesia was calculated as percent maximum possible effect by expressing the ratio (test latency−control latency)/(10-s control latency) as a percentage (Compton, D. R., et al., *J. Pharmacol. Exp. Ther.,* 260:201–209 (1992)). Ambient temperature was kept between 20 and 22° C. Values have been expressed as means and limits of error as standard errors. Dunnett's test has been used to calculate the significance of differences between the mean effect of each drug treatment and the mean effect of the vehicle, Tween 80.

Figure 4:
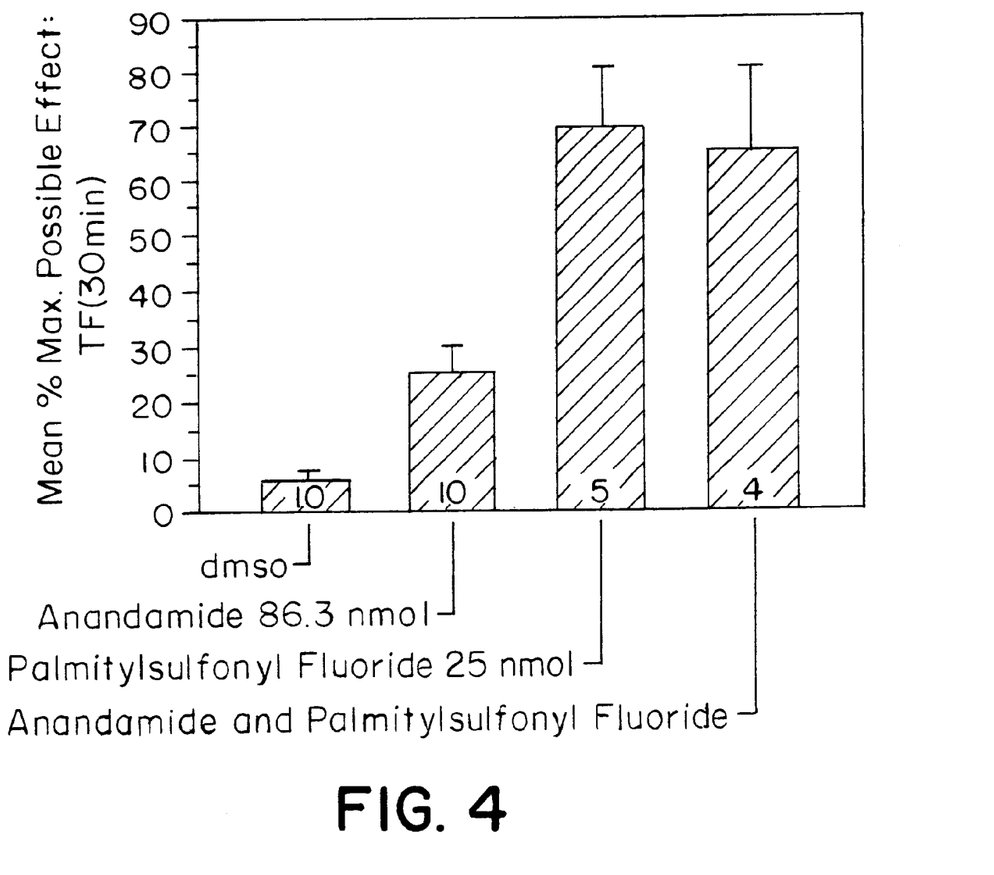
FIG. 4 is a graph showing the effect in rats of anandamide, palmitylsulfonyl fluoride and anandamide co-administration of palmitylsulfonyl fluoride on the time taken for a lightly restrained mouse to flick its tail away from radiant heat stimulus ("rat flick" test), measured by the percent maximum possible effect.

The results are shown in FIG. 4. Palmitylsulfonyl fluoride and anandamide co-administered with palmitylsulfonyl fluoride were about 3× more effective at producing analgesia in the mice than anandamide alone and about 13× more effective than the vehicle.

Example 5

Alkylsulfonyl Fluorides

Alkylmagnesium bromide in dry ether was added to a stirred solution of sulfuryl chloride (2-fold excess) in hexane at 0° C. The reaction mixture was stirred for 1 hour at 0° C. and then the ice bath was removed and stirring was continued overnight at room temperature. The solvent was evaporated in vacuo and the product was purified with column chromatography on silica gel to afford the corresponding alkylsulfonyl chloride as white solid.

Alkylsulfonyl chloride was dissolved in acetone and a 10-fold excess of ammonium fluoride was added while stirring at room temperature. The reaction mixture was refluxed for 3 hours. Then it was filtered to remove the insoluble salt, the solvent was evaporated and the product was dried in vacuo. Water was added to hydrolyze any unreacted alkylsulfonyl chloride and the aqueous mixture was extracted with ether. The ethereal extracts were combined, dried, filtered and the solvent was removed in vacuo. The product was purified with column chromatography on silica gel to afford the corresponding alkylsulfonyl fluoride.

Example 6

Alkyl-N-[alkyl-sulfonyl)oxy] Succinimides

Stobbe condensation of aldehydes with diethylsuccinate affords the corresponding alkenylsuccinic acid monoethyl esters which are catalytically hydrogenated and subsequently hydrolyzed to give the corresponding alkylsuccinic acids. The acids are mixed with excess of acetic anhydride and refluxed for 1 hour. The excess of acetic anhydride is removed in vacuo. Vacuum distillation affords the pure alkylsuccinic anhydrides.

The pure products are dissolved in dry toluene and brought to reflux. An equimolar amount of (benzyloxy) amine in toluene is added and the mixtures are refluxed for 30 minutes. The hot solutions are filtered through anhydrous sodium sulfate and the solvent is removed on a rotary evaporator. The residues are dissolved in ethyl acetate and washed with 10% sodium bicarbonate twice and then purified with column chromatography on silica gel.

The resulting 3-alkenyl-N-(benzyloxy)succinimides are hydrogenolyzed with 10% Pd—C for 3 hours. The reaction mixtures are then filtered through a Celite pad and the solvent removed in vacuo. The produced 3-alkyl-N-hydroxysuccinimides are then dissolved in dry toluene and treated with dry pyridine and various alkylsulfonyl chlorides. The reactions are stirred overnight at room temperature under nitrogen and then quenched with the addition of 2N HCl. The products are extracted with ethyl acetate (twice), dried over anhydrous $MgSO_4$ and purified with column chromatography.

Example 7

N-O-diacylhydroxylamines

Methyl esters of various carboxylic acids are treated with excess of hydroxylamine in methanol. Equimolar amounts of KOH and various acid chlorides dissolved in THF are added to aqueous solutions of the hydroxamic acids at 0–5° C. in order to afford the corresponding N,O-diacylhydroxylamines.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A method for inducing analgesia in an individual or animal comprising administering to the individual or animal a therapeutically effective amount of a compound to induce analgesia; wherein the compound is represented by the following structural formula:

R—X—Y and physiologically acceptable salts thereof, wherein:
R is selected from the group consisting of a methyl group, an aryl group, a substituted aryl group, a heteroaryl group, a substituted heteroaryl group, a heterocyclic group and a substituted heterocyclic group;

X is a straight chain hydrocarbyl group or a substituted straight chain hydrocarbyl group containing from about 4 to about 18 carbon atoms if R is an aryl group, a substituted aryl group, a heteroaryl group, a substituted heteroaryl group, a heterocyclic group or a substituted heterocyclic group;

X is a straight chain hydrocarbyl group or a substituted straight chain hydrocarbyl group containing from about 10 to about 24 carbon atoms if R is a methyl group; and Y is selected from the group consisting of:

wherein:
R1 is selected from the group consisting of —F and O—$C_{1-4}$ alkyl group wherein the alkyl group may be straight or branched chain; and R2 is a C1 to C4 straight or branched chain alkyl group.

2. The method of claim 1 wherein Y is —$SO_2$—O—$C_{1-4}$ alkyl group wherein the alkyl group may be straight or branched chain.

3. The method of claim 1 wherein Y is —$SO_2OCH_3$.

4. The method of claim 3 wherein R—X— is:

5. The method of claim 3 wherein R—X— is $CH_3$—$(CH_2)_n$—, wherein n is an integer from 10 to about 24.

6. The method of claim 1 wherein Y is —$SO_2F$.

7. The method of claim 6 wherein R—X— is:

8. The method of claim 6 wherein R—X— is $CH_3$—$(CH_2)_n$—, wherein n is an integer from 10 to about 24.

9. The method of claim 8 wherein n is 14.

10. A method for increasing anandamide levels in an individual or animal comprising administering to the individual or animal a therapeutically effective amount of a compound to increase anandamide levels; wherein the compound is represented by the following structural formula:

R—X—Y and physiologically acceptable salts thereof, wherein:
R is selected from the group consisting of a methyl group, an aryl group, a substituted aryl group, a heteroaryl group, a substituted heteroaryl group, a heterocyclic group and a substituted heterocyclic group;

X is a straight chain hydrocarbyl group or a substituted straight chain hydrocarbyl group containing from about 4 to about 18 carbon atoms if R is an aryl group, a substituted aryl group, a heteroaryl group, a substituted heteroaryl group, a heterocyclic group or a substituted heterocyclic group;

X is a straight chain hydrocarbyl group or a substituted straight chain hydrocarbyl group containing from about 10 to about 24 carbon atoms if R is a methyl group; and Y is selected from the group consisting of:

wherein:
R1 is selected from the group consisting of —F and O—$C_{1-4}$ alkyl group wherein the alkyl group may be straight or branched chain; and
R2 is a C1 to C4 straight or branched chain alkyl group.

11. The method of claim 10 wherein Y is —$SO_2$—O—$C_{1-4}$ alkyl group wherein the alkyl group may be straight or branched chain.

12. The method of claim 10 wherein Y is —$SO_2OCH_3$.

13. The method of claim 12 wherein R—X— is:

14. The method of claim 12 wherein R—X— is $CH_3$—$(CH_2)_n$—, wherein n is an integer from 10 to about 24.

15. The method of claim 10 wherein Y is —$SO_2F$.

16. The method of claim 15 wherein R—X— is:

17. The method of claim 15 wherein R—X— is $CH_3$—$(CH_2)_n$—, wherein n is an integer from 10 to about 24.

18. The method of claim 17 wherein n is 14.

* * * * *